United States Patent
Placa, Jr. et al.

(10) Patent No.: US 11,077,990 B2
(45) Date of Patent: Aug. 3, 2021

(54) PACKAGING SYSTEM FOR MEDICATED STARCH-BASED POWDER FORMULATIONS

(71) Applicant: Davion, Inc., North Brunswick, NJ (US)

(72) Inventors: James A. Placa, Jr., Morristown, NJ (US); James A. Placa, III, Hoboken, NJ (US)

(73) Assignee: Davion, Inc., North Brunswick, NJ (US)

( * ) Notice: Subject to any disclaimer, the term of this patent is extended or adjusted under 35 U.S.C. 154(b) by 0 days.

(21) Appl. No.: 15/851,024

(22) Filed: Dec. 21, 2017

(65) Prior Publication Data

US 2019/0193897 A1 Jun. 27, 2019

(51) Int. Cl.

| | | |
|---|---|---|
| *B65D 41/14* | (2006.01) | |
| *B65D 51/20* | (2006.01) | |
| *B65D 81/24* | (2006.01) | |
| *A61K 31/04* | (2006.01) | |
| *B29D 22/00* | (2006.01) | |
| *B65D 85/00* | (2006.01) | |
| *A61K 31/045* | (2006.01) | |
| *A61K 31/718* | (2006.01) | |
| *B29K 227/00* | (2006.01) | |

(Continued)

(52) U.S. Cl.
CPC ............ *B65D 41/14* (2013.01); *A61K 31/045* (2013.01); *A61K 31/718* (2013.01); *B29D 22/003* (2013.01); *B65D 51/20* (2013.01); *B65D 81/24* (2013.01); *B65D 85/70* (2013.01); *B29K 2223/06* (2013.01); *B29K 2227/06* (2013.01); *B29K 2227/08* (2013.01)

(58) Field of Classification Search
CPC ...... B65D 41/145; B65D 41/14; B65D 41/10; B65D 51/20; B65D 81/26; B65D 81/24; B65D 81/264; A61K 31/045; A61K 31/718; B29D 22/003; B29D 22/00
USPC ....... 215/346, 341, 261, 326, 324, 316, 232; 220/359.4, 359.1; 53/471, 467, 479, 478, 53/477; 206/528; 426/46; 424/46
See application file for complete search history.

(56) References Cited

U.S. PATENT DOCUMENTS 2,175,780 A * 10/1939 Prehn .................. A61K 9/0014
514/164
3,250,639 A * 5/1966 Stead ...................... C08J 7/047
428/349

(Continued)

OTHER PUBLICATIONS

Product literature for Fromonda AtoneMint Powder. Copyright 2017.

(Continued)

*Primary Examiner* — Robert J Hicks
(74) *Attorney, Agent, or Firm* — McCarter & English, LLP

(57) ABSTRACT

Medicated starch-based powder formulations are packaged to ensure the medication remains stable for a desired shelf life. The medicated starch-based powder formulation may be packaged in a sealed container so as to maintain medicament functionality for at least one year. The container may be fabricated and/or lined with a low permeability coefficient and sealed with a foil heat induction seal liner. The container may be treated with a media to alter the surface properties of the container to increase the integrity of the container. The medicated starch-based powder formulation may include cornstarch and menthol.

13 Claims, 3 Drawing Sheets

(51) Int. Cl.
*B29K 223/00* (2006.01)
*B29K 227/06* (2006.01)

(56) References Cited

U.S. PATENT DOCUMENTS

| | | | | |
|---|---|---|---|---|
| 3,275,203 A | * | 9/1966 | Nossal | B65B 7/168 |
| | | | | 156/253 |
| 3,767,076 A | * | 10/1973 | Kennedy | B29C 66/542 |
| | | | | 215/232 |
| 3,833,142 A | * | 9/1974 | Owen | B65D 41/20 |
| | | | | 215/337 |
| 4,013,188 A | * | 3/1977 | Ray | B29C 66/7234 |
| | | | | 215/347 |
| 4,118,480 A | * | 10/1978 | Williams | A61K 33/245 |
| | | | | 424/653 |
| 4,393,106 A | * | 7/1983 | Maruhashi | B29C 49/22 |
| | | | | 156/229 |
| 4,697,719 A | * | 10/1987 | Allen | B65D 43/0212 |
| | | | | 215/232 |
| 4,756,964 A | * | 7/1988 | Kincaid | B05D 1/62 |
| | | | | 156/272.6 |
| 4,801,030 A | * | 1/1989 | Barriac | B65D 41/3428 |
| | | | | 215/252 |
| 5,019,212 A | * | 5/1991 | Morita | A23L 3/3409 |
| | | | | 162/146 |
| 5,096,078 A | * | 3/1992 | McQueeny | B65D 51/26 |
| | | | | 206/522 |
| 5,143,763 A | * | 9/1992 | Yamada | A23L 3/3436 |
| | | | | 206/204 |
| 5,153,038 A | * | 10/1992 | Koyama | B32B 27/18 |
| | | | | 428/35.8 |
| 5,338,535 A | | 8/1994 | Berndt | |
| 5,397,573 A | * | 3/1995 | Kajs | A61K 9/4891 |
| | | | | 424/451 |
| 5,502,087 A | * | 3/1996 | Tateosian | A61C 13/20 |
| | | | | 433/168.1 |
| 8,348,079 B2 | * | 1/2013 | Baird-Smith | B65D 43/0231 |
| | | | | 220/258.1 |
| 2003/0009674 A1 | * | 5/2003 | Chen | A61K 31/7048 |
| | | | | 424/400 |
| 2006/0183804 A1 | * | 8/2006 | Brinkman | A61K 31/198 |
| | | | | 514/567 |
| 2007/0023381 A1 | * | 2/2007 | Cerveny | B65D 51/2821 |
| | | | | 215/228 |
| 2007/0014719 A1 | | 12/2007 | Reading et al. | |
| 2009/0297566 A1 | | 12/2009 | Brinkman et al. | |
| 2010/0065528 A1 | * | 3/2010 | Hanafusa | B65D 41/045 |
| | | | | 215/347 |
| 2010/0168074 A1 | * | 7/2010 | Culligan | A61K 9/2027 |
| | | | | 514/197 |
| 2012/0282190 A1 | * | 11/2012 | Hammer | A61K 8/046 |
| | | | | 424/47 |
| 2016/0031623 A1 | * | 2/2016 | Staffers | B65B 7/168 |
| | | | | 220/214 |

OTHER PUBLICATIONS

Product literature for Safety Aluminium Foil Seals, https://www.indiamart.com/proddetail/safety-aluminium-foil-seals-9375333897.html; downloaded on Oct. 4, 2017.
Product literature for Peppermint Essential Oil Dusting Powder, https://www.etsy.com/listing/531334244/peppermint-essential-oil-dusting-powder; downloaded on Oct. 4, 2017.
Product literature for Induction Seal, Cap Liners, Induction Foil, https://www.seligsealing.com/product/product/index/id/75.html; downloaded on Oct. 4, 2017.
Product literature for Aluminium Foil Seals, https://www.indiamart.com/proddetail/aluminium-foil-seals-6713388691.html; downloaded on Oct. 4, 2017.
Product literature for Induction Sealing Wads, https://www.indiamart.com/proddetail.induction-sealing-wads-15959383597.html; downloaded on Oct. 4, 2017.

* cited by examiner

PACKAGING SYSTEM FOR MEDICATED STARCH-BASED POWDER FORMULATIONS

BACKGROUND

1. Technical Field

This invention relates to medicated starch-based powder formulations that are packaged to ensure that the medication remains stable/effective for a desired shelf life.

2. Background Art

It is understood that a powder formulation for personal use may be medicated or unmedicated. Traditional topical powder formulations frequently include talcum powder and one or more additional ingredients to provide desired functionalities. Recently, however, uncertainty surrounding health impacts from utilizing talcum powder in topical powders has increased attention on topical formulations that omit talcum powder.

Starch-based topical formulations, e.g., formulations that include cornstarch rather than talcum powder, may provide similar functionalities to talc-based formulations in unmedicated applications. Conversely, medicated cornstarch-based powder formulations falter relatively quickly as a result of difficulty in sustaining medicated functionalities for a desired/required period of time. For example, topical formulations that include corn starch and menthol constituents generally suffer from unacceptably rapid loss of medicament functionality when packaged using conventional topical powder packaging systems. Traditional powder packaging utilizes polymer-based containers, e.g., containers fabricated using low density polyethylene ("LDPE"), high density polyethylene ("HDPE"), polypropylene ("PP"). In addition, conventional packaging systems for topical formulations include caps that are screw-on/snap-on to the underlying container for ease of powder application.

Menthol is routinely incorporated into topical powder formulations to cool and soothe irritated skin, protect the skin, and also provide odor control. Menthol, in its crystalline form, melts at a temperature of 31° C., only slightly higher than room temperature. In addition, menthol has a low flash point of 38° C., which may cause the menthol to dissipate and evaporate into the atmosphere with undesirable ease. As a result, as mentioned above, medicated topical powders traditionally have been produced with a talc-based formulation, leveraging the ability of the talc to slow down the dissipation and evaporation of the menthol from the system.

In cornstarch-based powder formulations with menthol, unlike in the talc-based powder formulation with menthol, the physical nature of menthol and the hygroscopic nature of cornstarch creates a high vapor pressure and accelerates flashing of the menthol, thereby significantly reducing the shelf life of a cornstarch-based powder formulation with menthol.

Based on the foregoing, a need exists for topical formulations that eliminate talcum powder as a base ingredient, but that provide effective medicament functionality over a desired period of time, e.g., at least one year. In addition, a need exists for packaging systems that permit packaging of topical formulations that eliminate talcum powder as a base ingredient, and that provide effective medicament functionality over a desired period of time, e.g., at least one year.

These and other needs are satisfied by the formulations/packaging systems disclosed herein.

SUMMARY

Exemplary embodiments of the present disclosure include packaged medical formulations for topical use that eliminate talcum powder and that maintain medicament functionality over a desired timeframe, e.g., at least one year. Exemplary embodiments of the present disclosure include topical formulations that include corn starch and a medicament, e.g., menthol, and that are packaged so as to reduce dissipation of the medicament and maintain desired medicament functionality for a desired period, e.g., at least one year.

In exemplary embodiments, the packaging system includes a container for housing the disclosed formulation and a cover to seal the container. The container may take various forms, e.g., a bottle, a pouch, a flask, a jar, a jug, a bag, a tube, a cylinder, or any combination thereof. In an exemplary embodiment, the container is a bottle that is fabricated from a material with a low permeability coefficient, e.g., polyethylene terephthalate ("PET"), polyethylene terephthalate with glycol ("PETG"), polyvinyl chloride ("PVC"), polyvinylidene chloride ("PVDC"), or a combination thereof. In another exemplary embodiment, the container may be treated with and/or lined with a material with a low permeability coefficient, e.g., PET, PETG, PVC, PVDV, or a combination thereof. Treatment of the container may occur simultaneous with fabrication of the container and/or after the fabrication of the container, i.e., as a post-fabrication treatment.

Once the disclosed medicated topical formulation that excludes talcum powder is introduced to the container, e.g., using conventional packaging techniques, the opening of the container is generally sealed to provide a sealed enclosure. Exemplary sealing methods include applying a foil seal liner to the container opening using heat induction. The foil seal provides a tight seal to the container and reduces the loss of medicament, e.g., menthol, through flashing. To further ensure a tight seal and to protect the liner from puncture, a screw-on or snap-on cover may be applied to the top of the container to encase the liner between the top edge of the container and the inside face of the cover. The noted cover may also facilitate use of the medicated powder, e.g., through a "sift-top" opening or the like.

Additional features, functions and benefits of the disclosed medicament-containing formulations and packaging systems will be apparent from the description which follows, particularly when read in conjunction with the accompanying figure(s).

BRIEF DESCRIPTION OF DRAWINGS

Illustrative embodiments are shown by way of example in the accompanying figures and should not be considered as a limitation of the present disclosure.

DETAILED DESCRIPTION OF THE DRAWINGS

Figure 1:
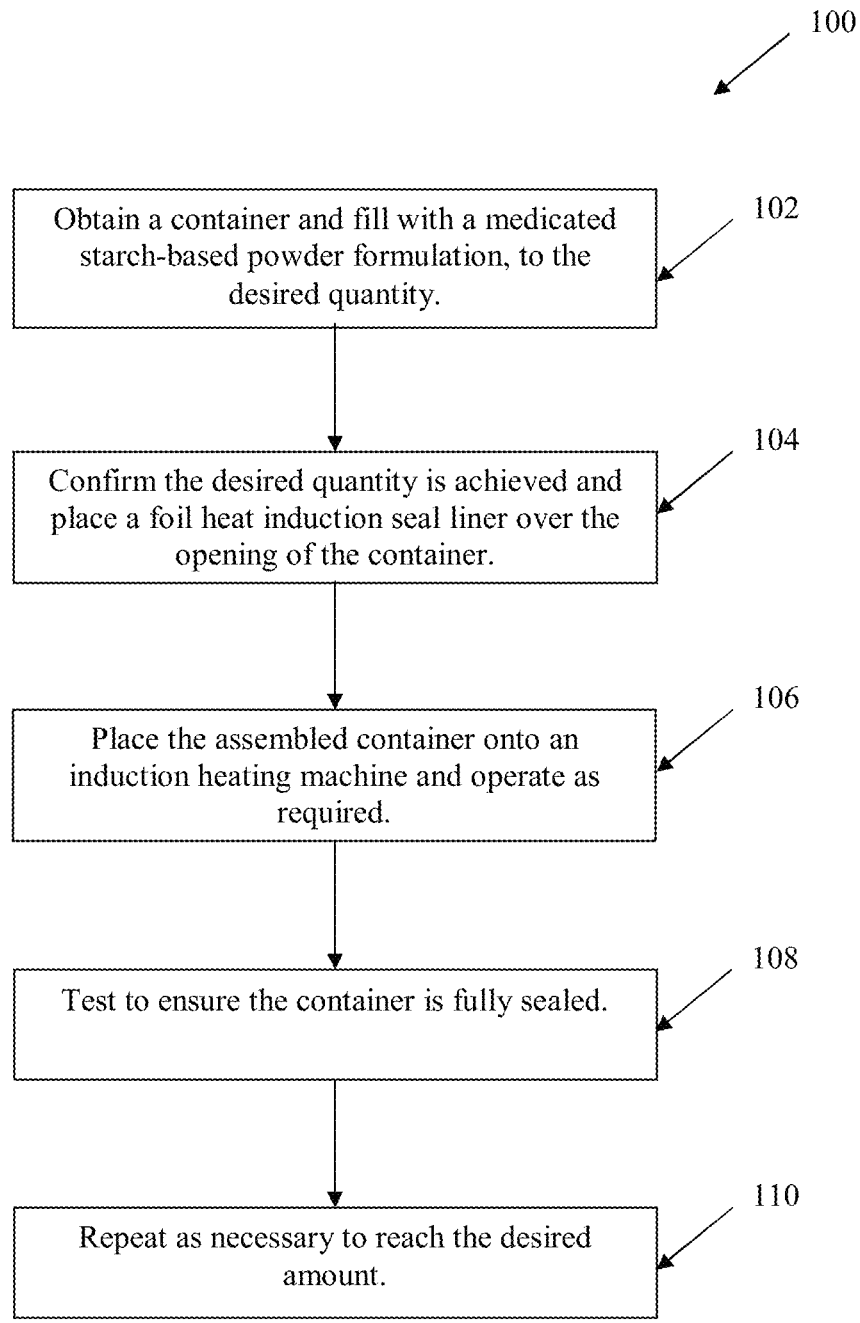
FIG. 1 depicts a process flow chart for packaging medicament-containing powders according to the present disclosure.

Exemplary embodiments of the present disclosure include packaging systems for reducing dissipation and evaporation of a medication, e.g., menthol, when combined with a starch-based, e.g., cornstarch, powder formulation for topical use. In an exemplary embodiment, the packaging includes a container for housing a powder and a cover to seal the container. The container may also include labeling that sets forth a description of the product, the dosage amount, the quantity, among other informative details concerning the product, as required or desired. Although the following embodiments may only highlight one or more specific containers when describing the details of the disclosed packaging systems, the embodiments are merely for illustrative purposes and the present disclosure is not limited by or to only those containers mentioned.

In order to reduce the permeation of a medicament (e.g., menthol) and extend the shelf life for a medicated cornstarch-based powder formulation according to the present disclosure, a container including a material with a low permeability coefficient is preferred. In an illustrious embodiment, the oxygen permeability range is 0.1 cc/100 square inches to 400 cc/100 square inches. More preferably, the oxygen permeability range is 0.1 cc/100 square inches to 200 cc/100 square inches. The container may be fabricated from and/or coated/lined with PET, PETG, PVC, PVDC, nylon-6, or a combination thereof. In an exemplary embodiment, the container is treated with a media that alters the surface properties of the container (e.g., inside and outside surfaces) to increase the integrity of the container (e.g., reduce permeation). Treatment may be applied to conventional plastics (e.g., not high performance plastics) to transform the plastic into a high performance plastic (e.g., a plastic with a low permeability coefficient). The opening of the container is generally sealed to provide shelf stability to the powder formulation, e.g., by way of a foil heat induction seal liner, which tightly seals the container and reduces the loss of medicament (e.g., menthol) through flashing. The liner may further include a tab for easy tear-off by the consumer.

To further ensure a tight seal and to protect the liner from puncture, a screw-on or snap-on cover may encase the liner between the top edge of the container and the inside face of the cover. The cover may be rigid or flexible and may further include child restraint features. The combination of a container that includes (i.e., fabricated, treated and/or coated/lined with) one or more materials with a low permeability coefficient, sealed with the foil heat induction seal liner, and capped with a cover, has been shown to be effective in maintaining medicament functionality in a cornstarch-based powder for a desired period of time, e.g., for at least one year.

In another embodiment, the container that stores the cornstarch-based powder formulation with a medicament (e.g., menthol) may take the form of a bag that is sealed using traditional bag-sealing methods, e.g., heat-sealing. In order to reduce the permeation of a medicament through the bag, the bag is advantageously fabricated from and/or coated/lined with a material that has a low permeability coefficient, e.g., PET, PETG, PVC, PVDC, nylon-6, or a combination thereof. In an exemplary embodiment, the container is treated with a media that alters the surface properties of the container (e.g., inside and outside surfaces) to increase the integrity of the container (e.g., reduce permeation), as discussed above. In an illustrious embodiment, the oxygen permeability range is 0.1 cc/100 square inches to 400 cc/100 square inches. More preferably, the oxygen permeability range is 0.1 cc/100 square inches to 200 cc/100 square inches. The combination of a container that includes (e.g., fabricated, treated, and/or coated/lined with) one or more materials with a low permeability coefficient, and sealed by traditional bag-sealing methods, has been shown to be effective in maintaining medicament (e.g., menthol) functionality in a cornstarch-based powder for a desired period of time, e.g., for at least one year.

FIG. 1 depicts a process flow chart 100 outlining an exemplary method for filling and sealing a container with a medicated starch-based powder formulation according to the present disclosure. At step 102, a container is obtained and filled with a medicated starch-based powder formulation, to the desired quantity. The size and type of container chosen will depend on the desired quantity and the prospective market. At step 104, the desired quantity is confirmed and then a foil heat induction seal liner is applied over the opening of the container.

At step 106, the assembled container is placed onto an induction heating machine and operated as required.

At step 108, the container is tested to ensure that it is fully sealed. For example, this may require squeezing the container to ensure that none of the powder is released as a result of an unset foil heat induction seal liner.

At step 110, repeat the above-described steps as necessary to achieve the desired amount of assembled containers.

In order to ensure a tight seal, a screw-on or snap-on cover may be tightened onto the container, thereby encasing the foil heat induction seal liner between the top edge of the container and the inside face of the cover.

Figure 2:
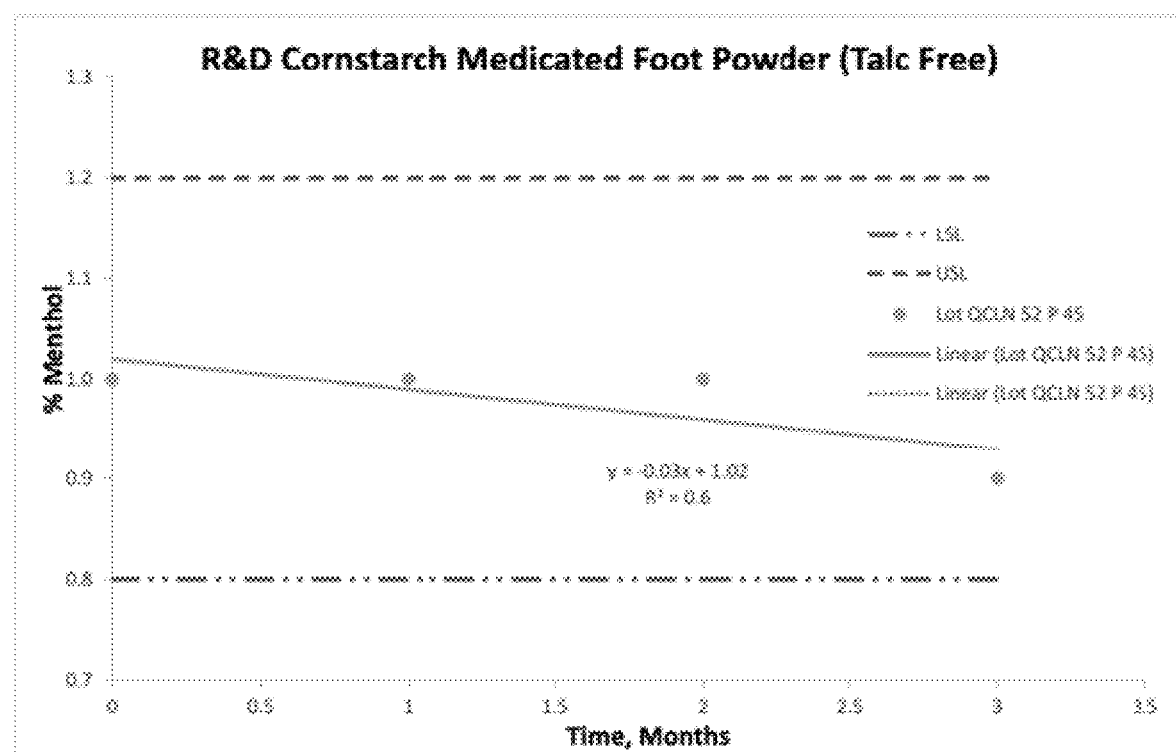
FIG. 2 is a plot of percent menthol and time for an experimental test according to the present disclosure.

FIG. 2 is a plot of percent menthol and time (in months) for a cornstarch-based medicated foot powder. The plot summarizes the results of an accelerated stability study conducted on the disclosed packaging over a three-month period of storage at 40° C. Based on linear regression calculations, the percent menthol would drop below the preferred range of percent menthol, i.e., 0.8%-1.2%, after month three at accelerated conditions. However, the three-month accelerated study is equivalent to 24 months of preferred storage conditions. Therefore, based on the percent menthol at accelerated storage conditions and linear regression, the packaging supports a 24-month expiration date.

Figure 3:
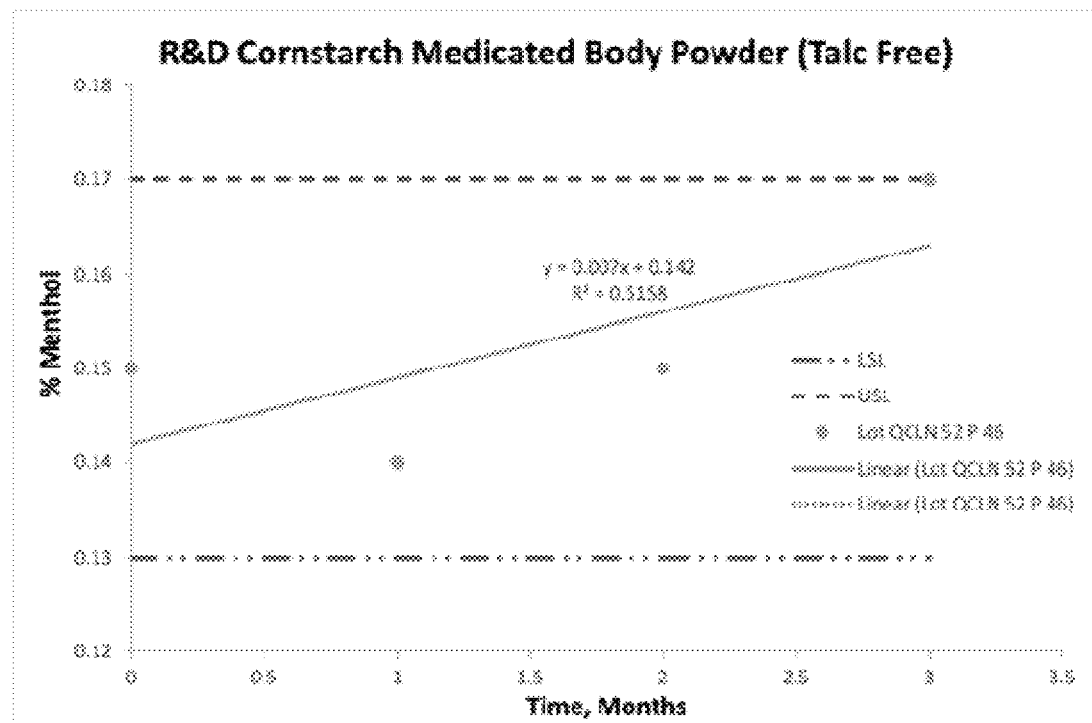
FIG. 3 is a plot of percent menthol and time for an experimental test according to the present disclosure.

FIG. 3 is a plot of percent menthol and time (in months) for cornstarch-based medicated body powder. The plot summarizes the results of an accelerated stability study conducted on the disclosed packaging over a three-month period of storage at 40° C. Based on linear regression calculations, the percent menthol would drop below the preferred range of percent menthol, i.e., 0.13%-0.17%, after month three at accelerated conditions. However, the three-month accelerated study is equivalent to 24 months of preferred storage conditions. Therefore, based on the percent menthol at accelerated storage conditions and linear regression, the packaging supports a 24-month expiration date.

The present embodiments are to be considered as merely illustrative and not restrictive and may be embodied in other specific forms without departing from the spirit or essential characteristics thereof.

The invention claimed is:

1. A packaged medicated powder, comprising:
   a powder formulation that includes (i) a starch, and (ii) menthol; and
   a packaging system consisting of:
      a container fabricated from a polymeric material, the container defining an opening and an internal container volume within which the powder formulation is positioned; and
      a foil heat induction seal liner mounted with respect to the opening of the container and sealing the container opening in the absence of a cover or cap;

wherein the polymeric material has a permeability coefficient that in combination with the foil heat induction seal liner ensures that menthol stability within the container is maintained for at least one year.

2. The packaged medicated powder of claim 1, wherein the container is fabricated from or lined with a material selected from the group consisting of PET, PETG, PVC, PVDC, nylon-6, and a combination thereof.

3. The packaged medicated powder of claim 1, wherein the container is selected from the group consisting of a bottle, a pouch, a flask, a jar, a jug, a bag, a tube, a cylinder, and any combination thereof.

4. The packaged medicated powder of claim 1, further comprising a cover that is screwed on or snapped on the sealed container.

5. The packaged medicated powder of claim 1, wherein the foil heat induction seal liner is applied to the container using a heat-sealing process.

6. The packaged medicated powder of claim 1, wherein the menthol is maintained at a level of at least 0.8% after twenty four months storage.

7. The packaged medicated powder of claim 1, wherein the starch is cornstarch.

8. The packaged medicated powder of claim 1, wherein the container is treated with a media to alter the surface properties of the container.

9. A method of packaging a medicated starch-based powder, the method comprising:

providing a container fabricated from a polymeric material;

introducing a medicated starch-based powder formulation that includes menthol through an opening and into an internal volume of the container; and sealing the opening of the container solely by applying a foil heat induction seal liner over the opening of the container and in the absence of a cover or cap;

wherein the polymeric material has a permeability coefficient that in combination with the foil heat induction seal liner ensures that menthol stability within the container is maintained for at least one year.

10. The method of packaging a medicated starch-based powder of claim 9, wherein the container is selected from the group consisting of a bottle, a pouch, a flask, a jar, a jug, a bag, a tube, a cylinder, and any combination thereof.

11. The method of packaging a medicated starch-based powder of claim 9, further comprising screwing or snapping a cover onto the sealed container.

12. The method of packaging a medicated starch-based powder of claim 9, wherein the container is fabricated from or lined with a material selected from the group consisting of PET, PETG, PVC, PVDC, nylon-6, and a combination thereof.

13. The method of packaging a medicated starch-based powder of claim 9, wherein the container is treated with a media to alter the surface properties of the container.

\* \* \* \* \*